United States Patent
Stumpo et al.

(10) Patent No.: US 7,628,794 B2
(45) Date of Patent: Dec. 8, 2009

(54) PROSTHETIC REVISION KNEE SYSTEM

(75) Inventors: David J. Stumpo, Venetia, PA (US); Donald A. Stevens, Spring Church, PA (US); Scott Jones, McMurray, PA (US)

(73) Assignee: Trigon Inc., McMurray, PA (US)

( * ) Notice: Subject to any disclaimer, the term of this patent is extended or adjusted under 35 U.S.C. 154(b) by 462 days.

(21) Appl. No.: 11/100,349

(22) Filed: Apr. 6, 2005

(65) Prior Publication Data
US 2006/0241635 A1  Oct. 26, 2006

(51) Int. Cl.
*A61B 17/58* (2006.01)
(52) U.S. Cl. .......................... 606/88; 606/86 R; 606/87
(58) Field of Classification Search .............. 623/20.14, 623/20.15, 20.35, 20.36; 606/86–88
See application file for complete search history.

(56) References Cited

U.S. PATENT DOCUMENTS

| | | | |
|---|---|---|---|
| 4,759,350 A * | 7/1988 | Dunn et al. .................... 606/82 |
| 5,002,545 A * | 3/1991 | Whiteside et al. ............. 606/80 |
| 5,053,037 A | 10/1991 | Lackey |
| 5,092,869 A | 3/1992 | Waldron |
| 5,100,408 A | 3/1992 | Lackey |
| 5,326,359 A | 7/1994 | Oudard |
| 5,405,395 A | 4/1995 | Coates |
| 5,417,694 A | 5/1995 | Marik et al. |
| 5,443,518 A * | 8/1995 | Insall ........................ 623/20.21 |
| 5,569,261 A | 10/1996 | Marik et al. |
| 5,624,444 A * | 4/1997 | Wixon et al. .................. 606/88 |
| 5,681,316 A | 10/1997 | DeOrio et al. |
| 5,683,397 A | 11/1997 | Vendrely et al. |
| 5,716,361 A * | 2/1998 | Masini ......................... 606/86 |
| 5,720,752 A | 2/1998 | Elliott et al. |
| 5,879,391 A | 3/1999 | Slamin |
| 6,033,410 A | 3/2000 | McLean et al. |
| 6,056,756 A | 5/2000 | Eng et al. |
| 6,071,311 A | 6/2000 | O'Neil et al. |
| 6,096,043 A | 8/2000 | Techiera et al. |
| 6,106,529 A | 8/2000 | Techiera |
| 6,258,095 B1 | 7/2001 | Lombardo et al. |
| 6,558,391 B2 * | 5/2003 | Axelson et al. ............... 606/88 |
| 6,740,092 B2 | 5/2004 | Lombardo et al. |
| 2001/0001121 A1 * | 5/2001 | Lombardo et al. ............ 606/89 |
| 2003/0204264 A1 * | 10/2003 | Stumpo et al. ........... 623/20.36 |
| 2005/0283249 A1 * | 12/2005 | Carson .................... 623/20.14 |

OTHER PUBLICATIONS

David J. Stumpo et al., *Stelkast Proven Constrained/Revision Knee*, Sep. 2004.

* cited by examiner

*Primary Examiner*—Eduardo C Robert
*Assistant Examiner*—Julianna N Harvey
(74) *Attorney, Agent, or Firm*—The Webb Law Firm (57) ABSTRACT

The present invention provides a femoral component, and a method for surgical implantation of a femoral prosthesis, comprised of a revision knee implant and corresponding cutting block system. In particular, the revision knee implant, comprised of a femoral component having incremental markings thereon and a femoral stem, and corresponding cutting block system having corresponding incremental markings thereon, enables a surgeon maximally to position the cutting block adjacent as much area as possible of a distal femur of a patient and to infinitely position the femoral component in the exact position indicated by the cutting block.

15 Claims, 7 Drawing Sheets

A perspective view of a bushing and femoral stem affixed onto an engagement surface of a femoral component.

Fig. 1. A perspective view of a bushing and femoral stem affixed onto an engagement surface of a femoral component.

Fig. 2. A perspective view of an embodiment of a femoral component (2A) and of a femoral stem attached to a bushing (2B)

Fig. 3. A side view of a femoral component having a bushing affixed thereon and a femoral stem attached to the bushing (3A) and a front view of a femoral component having a bushing affixed thereon and a femoral stem attached to the bushing (3B).

Fig. 4. An exploded front view of a bushing (4A); an end view of a base portion of a bushing (4B); and an exploded perspective view of a set screw (4C)

Fig. 5. A perspective view of a front section of a cutting block having a trial stem attached thereto.

Fig. 6. A perspective view of a back section of a cutting block having a trial stem attached thereto.

Fig. 7. A side view of a cutting block having a trial stem attached thereto.

PROSTHETIC REVISION KNEE SYSTEM

BACKGROUND OF THE INVENTION

1. Field of the Invention

The present invention relates to revision knee implants and surgical orthopedic cutting instruments, and more particularly relates to an improved revision knee femoral prosthesis and corresponding improved cutting block apparatus for shaping a distal femur of a patient prior to implantation of the femoral prosthesis.

2. Description of Related Art

In patients who require a revision knee system implant, there typically is much bone loss, and thus a lack of normal bony reference points or landmarks for properly aligning the implant. In these cases, surgeons use the intramedullary canal of the femur as a landmark for positioning the prosthesis. If the femoral stem of the implant is not properly aligned with respect to the intramedullary canal in the anterior-posterior direction, there will be a gap between the natural femur and the femoral component at the anterior or posterior end.

A conventional knee prosthesis generally has a smooth continuous outer curvature that faces a corresponding component attached to the patient's tibia, and includes a femoral component, a femoral stem, a patellar component and a tibial component. The femoral component typically includes a pair of spaced apart condylar portions that articulate with the tibial component. Additionally, the femoral component usually has an intercondylar surface located between the two condylar portions. The femoral stem typically is connected to the intercondylar surface of the femoral component by means of a bolt that passes through a bore in the intercondylar surface. The femoral stem is, in use, inserted into a reamed intramedullary canal of the femur. The patellar component articulates with the anterior surface of the femoral component.

Conventional revision knee prostheses come in various sizes and shapes to compatibly match the anatomical constraints of a variety of individual patients. Additionally, to further match a particular patient's anatomy, the femoral stem of the prosthesis typically is set at an angle, from lateral to medial, to match the patient's valgus angle, which is the angle between the axis of the femoral shaft and an imaginary vertical line extending from the distal femur to the center of the femoral head.

Before implanting a revision knee prosthesis, the distal femur of the patient needs to be surgically cut to allow for the proper alignment of the prosthesis implant. A typical femoral component of a knee prosthesis provides five intersecting flat surfaces. One surface is adapted to engage the anterior cortical surface of the femur. Another surface is adapted to face the posterior surface of the femur. Still another surface is adapted to engage the distal end of the patient's femur. Additionally, a pair of chamfer surfaces form diagonally extending surfaces which form an interface between the distal surface and the respective anterior and posterior surfaces.

Before beginning a cutting operation, the surgeon needs to orient a cutting guide in anterior and posterior directions relative to the patient's femur and also relative to the valgus angle of the patient's femur. A surgeon needs to form five separate cuts on the patient's distal femur in order to prepare the distal femur to receive the femoral prosthesis. One of the problems encountered by the surgeon is the proper orientation of the cuts so that the prosthesis will fit the femur with the correct orientation.

Conventional knee prostheses typically present with several notable shortcomings. For example, the anterior-posterior position of the femoral stem usually is not adjustable or only adjustable in limited increments, in both cases resulting in poor alignment of the femoral prosthesis with respect to the intramedullary canal of the femur or an unbalanced flexion gap, either of which can lead to deterioration of the implant. One typical revision knee system provides incremental anterior-posterior positioning by means of three interchangeable screw heads which permit limited variation of the anterior/posterior position from the norm, i.e., 0 mm, limited to increments of +3 and −3 mm. In another revision knee system, the femoral stem is attached to the femoral component by means of a nut and bolt. If the bolt loosens, it can migrate into the knee joint, resulting in injury to the surrounding tissue and damage to or interference with the prosthesis. Additionally, such nut and bolt systems can introduce particulate matter into the knee joint which can cause infection or lead to inflammatory immune responses.

Thus, there exists a need for a prosthetic revision knee system that allows for an infinite adjustment of the anterior/posterior position of the femoral stem to suit a wide range of patient anatomies, that permits a proper alignment of the valgus angle of the femoral stem in order to accommodate the anatomical constraints of a variety of patients, that optimizes the positioning of a femoral component and/or femoral stem vis a vis the available bone; and that provides a femoral stem locking system that will not migrate into the knee joint or cause damage to the articular surface of the implant which may lead to infection or inflammatory immune responses.

SUMMARY OF THE INVENTION

The present invention fulfills this need by providing a method for surgically implanting an improved revision knee femoral prosthesis utilizing an improved cutting block system for revision knee surgery in a patient, comprised of reaming the intramedullary canal of a distal femur of the patient to enlarge the intramedullary canal; inserting into the intramedullary canal a trial stem attached to a cutting block having a front surface and a back surface, in which the front surface has incremental markings thereon, wherein the trial stem is hingedly attached to the back surface of the cutting block by means of a threaded bolt therein, and further wherein the trial stem rotates laterally about 10 degrees around a longitudinal axis perpendicularly to the back surface of the cutting block to allow adaptability to a multitude of valgus angles. Adjusting the cutting block adjacent to a maximal area of the femur of the patient as possible by means of a screw that rotates the threaded bolt in order to raise or lower the cutting block in an anterior-posterior direction over the femur; noting the adjustment thus made on the front surface of the cutting block by determining the position of the trial stem by reading the incremental marking thereto; using the cutting block to cut the femur in order to fit a femoral component having corresponding incremental markings thereon; removing the cutting block and the trial stem from the femur; affixing a bushing to the same incremental marking position of the femoral component as read from the incremental marking of the cutting block; threadably attaching a femoral stem into the bushing; and implanting the femoral prosthesis to the distal femur of the patient. The invention also inheres in a femoral prosthesis comprising a femoral component having incremental markings thereon corresponding to incremental markings on the corresponding cutting block.

DETAILED DESCRIPTION OF THE INVENTION

The present invention provides a method for implanting an improved prosthetic revision knee utilizing an improved cutting block apparatus which allows for an infinite adjustment of the anterior/posterior position of a femoral stem to suit a wide range of patient anatomies, which permits a proper alignment of the valgus angle of the femoral stem in order to accommodate the anatomical constraints of a variety of patients, and which utilizes a femoral stem locking system that will not migrate into the knee joint.

FIGS. 1 through 7 illustrate various embodiments of the prosthetic revision knee and cutting block system utilized in the method of the present invention. The method of the present invention for surgically implanting a prosthetic revision knee implant 10 in a patient is comprised of a femoral component 15 and a femoral stem 20 which, when in use, are surgically implanted to a distal femur (not shown) which has been surgically prepared to accept the implant 10 by means of a cutting block 40, wherein the femoral component 15 and the cutting block 40 both have corresponding incremental markings 28, 58 thereon to achieve a proper alignment of the implant 10 with the distal femur of the patient.

Figure 5:
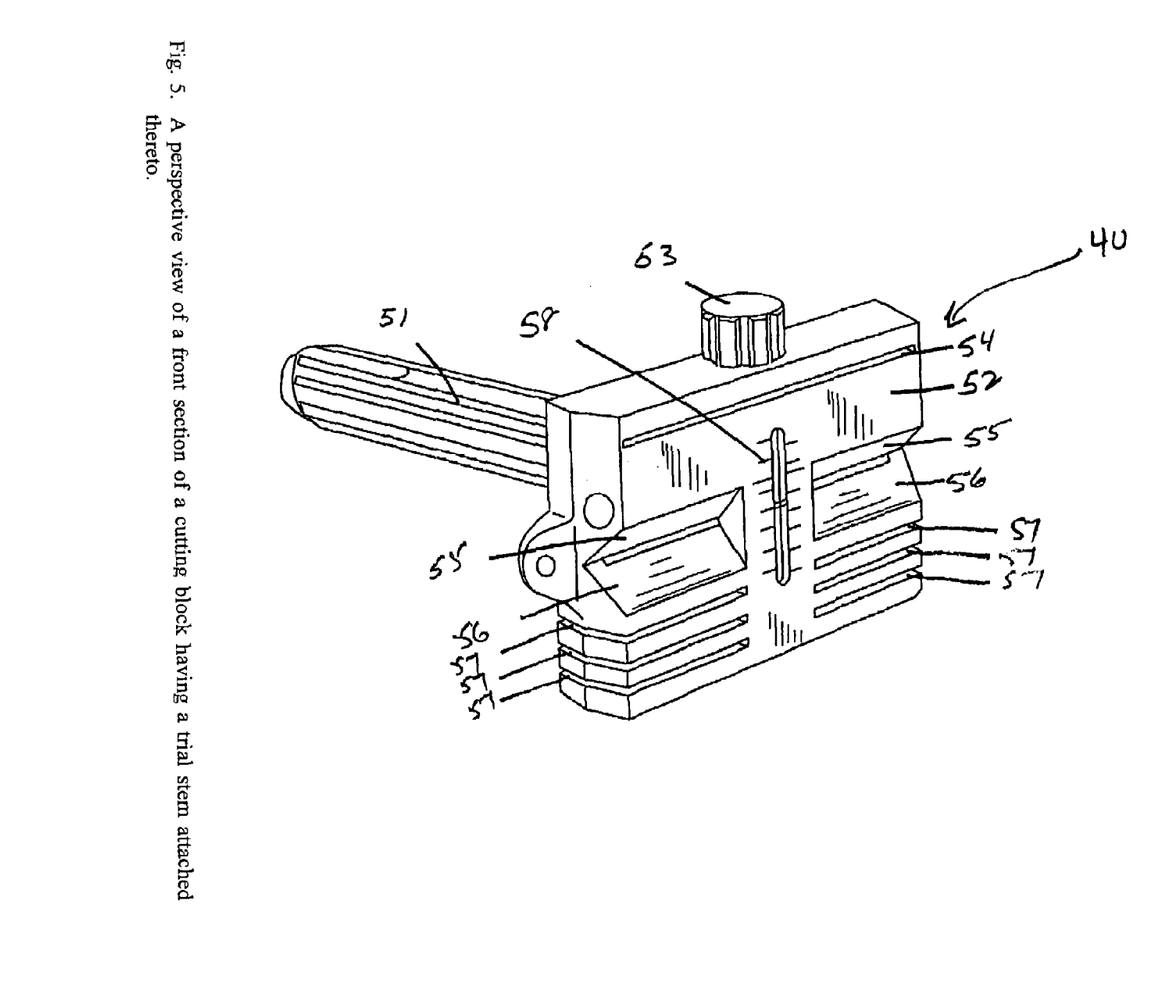
FIG. 5 is a perspective view of a front section of a cutting block having a trial stem attached thereto.
Figure 6:
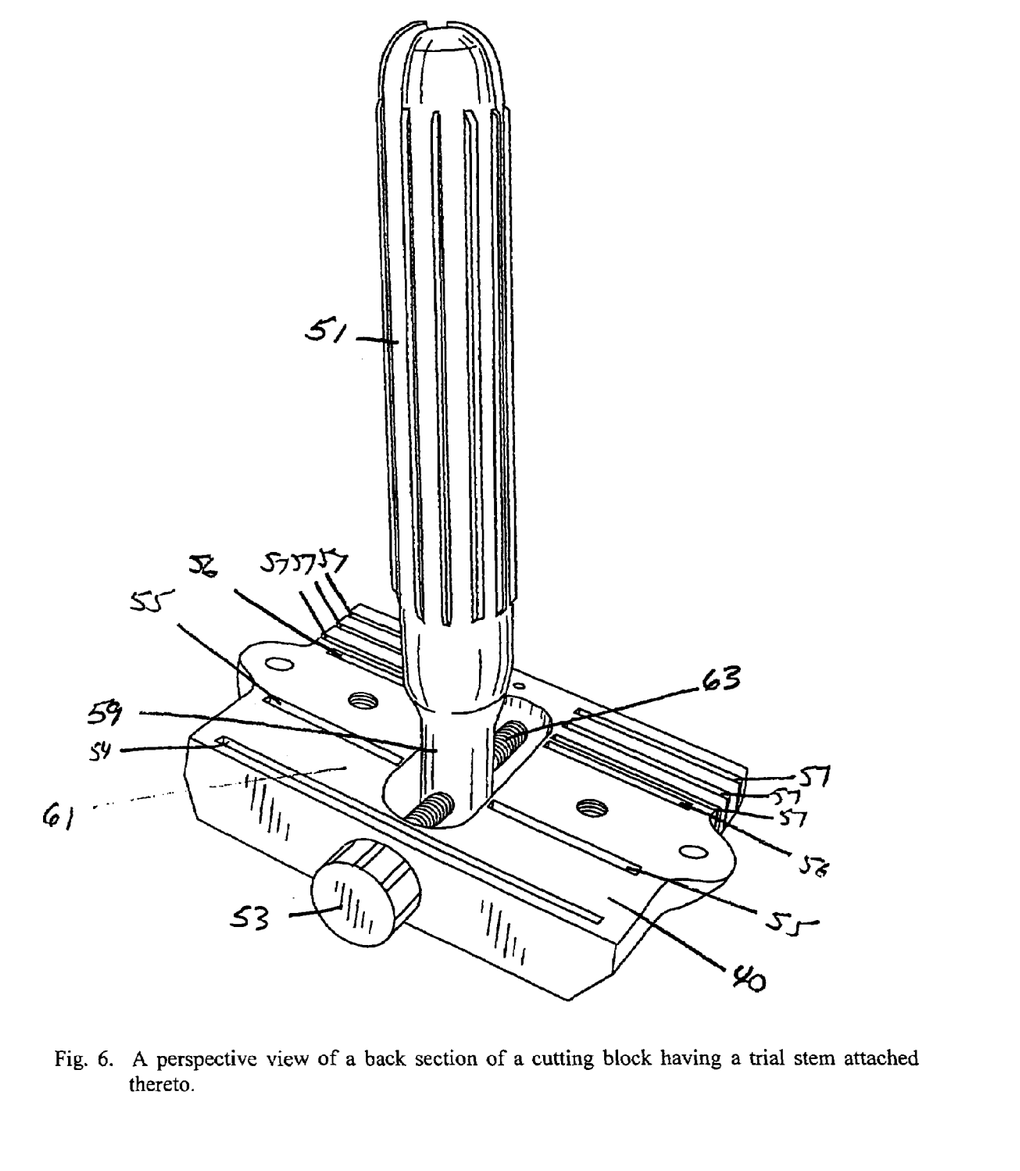
FIG. 6 is a perspective view of a back section of a cutting block having a trial stem attached thereto.
Figure 7:
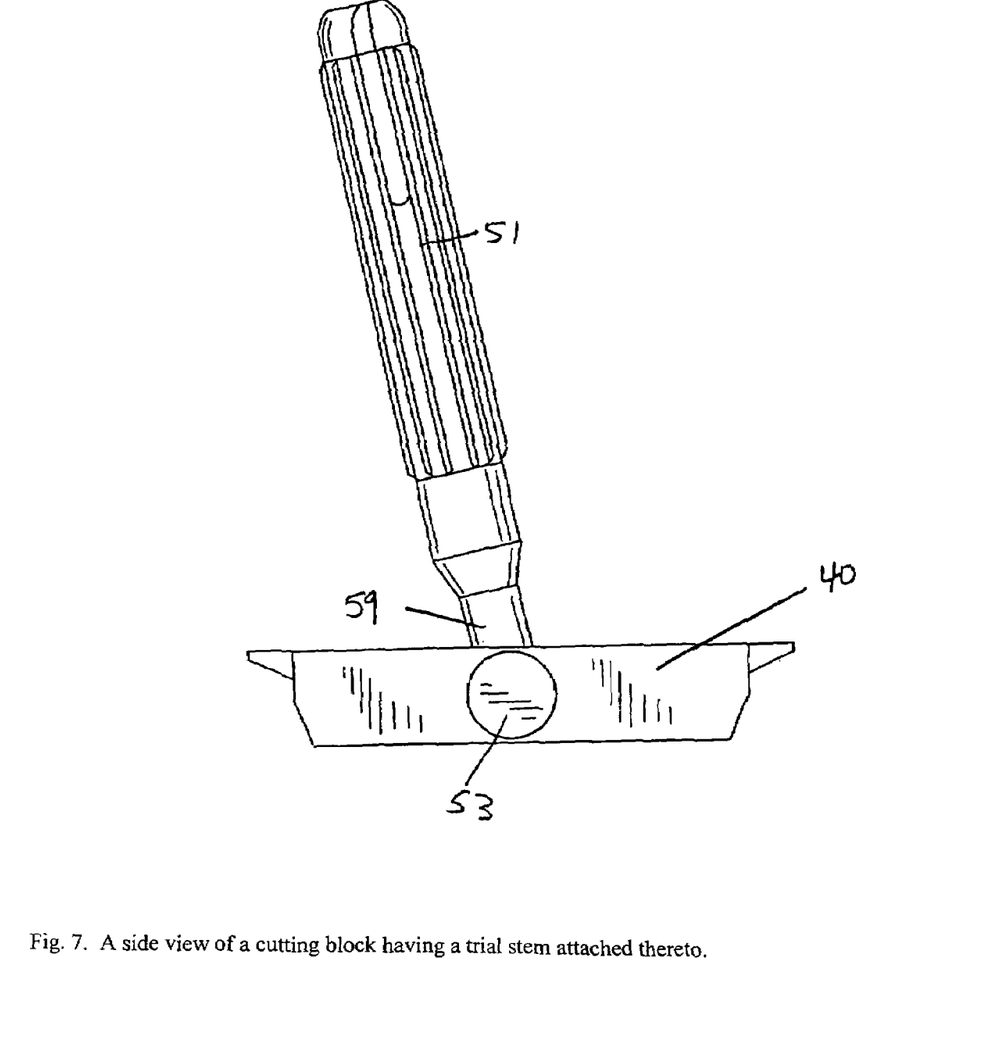
FIG. 7 is a side view of a cutting block having a trial stem attached thereto.

In particular, the method of the present invention provides for surgically implanting a prosthetic revision knee implant 10 which includes a femoral component 15 and a femoral stem 20 into a patient (FIG. 1), comprised of reaming the intramedullary canal of a distal femur of the patient to enlarge the intramedullary canal. As shown in FIGS. 5-7, a trial stem 51 is attached to a cutting block 40, which, when in use, is inserted into the intramedullary canal of a patient. The cutting block 40 has a front surface 52 (FIG. 5) and a back surface 61 (FIG. 6) in which the front surface 52 has incremental markings 58 thereon. The trial stem 51 is hingedly attached to the back surface 61 of the cutting block 40 by means of a cutting block bushing 59, in which the cutting block bushing 59 is threadably engaged to a threaded bolt 63 of the cutting block 40. The trial stem 51 rotates laterally about 10 degrees around a longitudinal axis perpendicular to the back surface 61 of the cutting block 40.

As part of the method of the present invention, the surgeon places the trial stem 51 attached to the cutting block 40 by means of the cutting block bushing 59 into the intramedullary canal of the patient's femur. The cutting block 40 then is positioned adjacent to as much available area as possible of the distal femur of the patient by adjusting the cutting block 40 position by means of an adjustment screw 53 which moves the cutting block 40 in an anterior-posterior direction by means of the threaded bolt 63.

As shown in FIG. 5, the front surface 52 of the cutting block 40 has incremental markings 58 thereon. The adjustment position of the cutting block 40 is noted by reading the value of the incremental marking 58 position of the cutting block 40 thus positioned. The front surface 52 of the cutting block has a plurality of cutting slots defined therein so as to allow the surgeon to make a plurality, and preferably four, separate cuts on the patient's distal femur in order to prepare the distal femur to receive the implant 10. In particular, the cutting slots are comprised of an anterior resection slot 54 that makes a flat cut on the anterior portion of the distal femur, an anterior chamfer slot 56 that makes an angled cut that corresponds to the angle of the femoral component 15, a posterior chamfer slot 55 that makes another angled cut that corresponds to another angle of the femoral component 15, and a plurality of posterior resection slots 57 that allow for one or more flat step resections of the posterior portion of the distal femur. After the resection and chamfer cuts are made, the trial stem 51 and the cutting block 40 are removed from the distal femur of the patient.

As shown in FIGS. 2A, 3A and 3B, the femoral component 15 has an anterior surface 21 and a posterior surface 22, and preferably has a pair of spaced-apart condylar portions 23 that define an intercondylar region 24. The condylar portions 23 allow the femoral component 15 to articulate with a tibial component (not shown). Additionally, the femoral component 15 is preferably symmetrical so that it can be used in either the right or left knee of the patient.

The intercondylar region 24 can have almost any length or width within the limitations of the femoral component 15 and within anatomical limitations of the patient. Preferably, the intercondylar region 24 spans the length of the femoral component 15 in the anterior-posterior direction. The intercondylar region 24 may vary in width. The intercondylar region 24 has an elongate engagement surface 25 extending in the anterior-posterior direction. The engagement surface 25 can be any shape or size of surface (within the limitations of the femoral component 15 and within anatomical limitations of the patient) which allows for complementary engagement with another surface. Preferably, the engagement surface 25 includes opposing rails 26. The engagement surface 25 preferably spans the entire length of the intercondylar region 24 to maximize the range of anterior/posterior offset of the femoral stem 20. The engagement surface 25, however, can span a shorter length of the intercondylar region 24 while still offering a range of anterior-posterior positioning not found in prior art revision knee systems.

Figure 4:
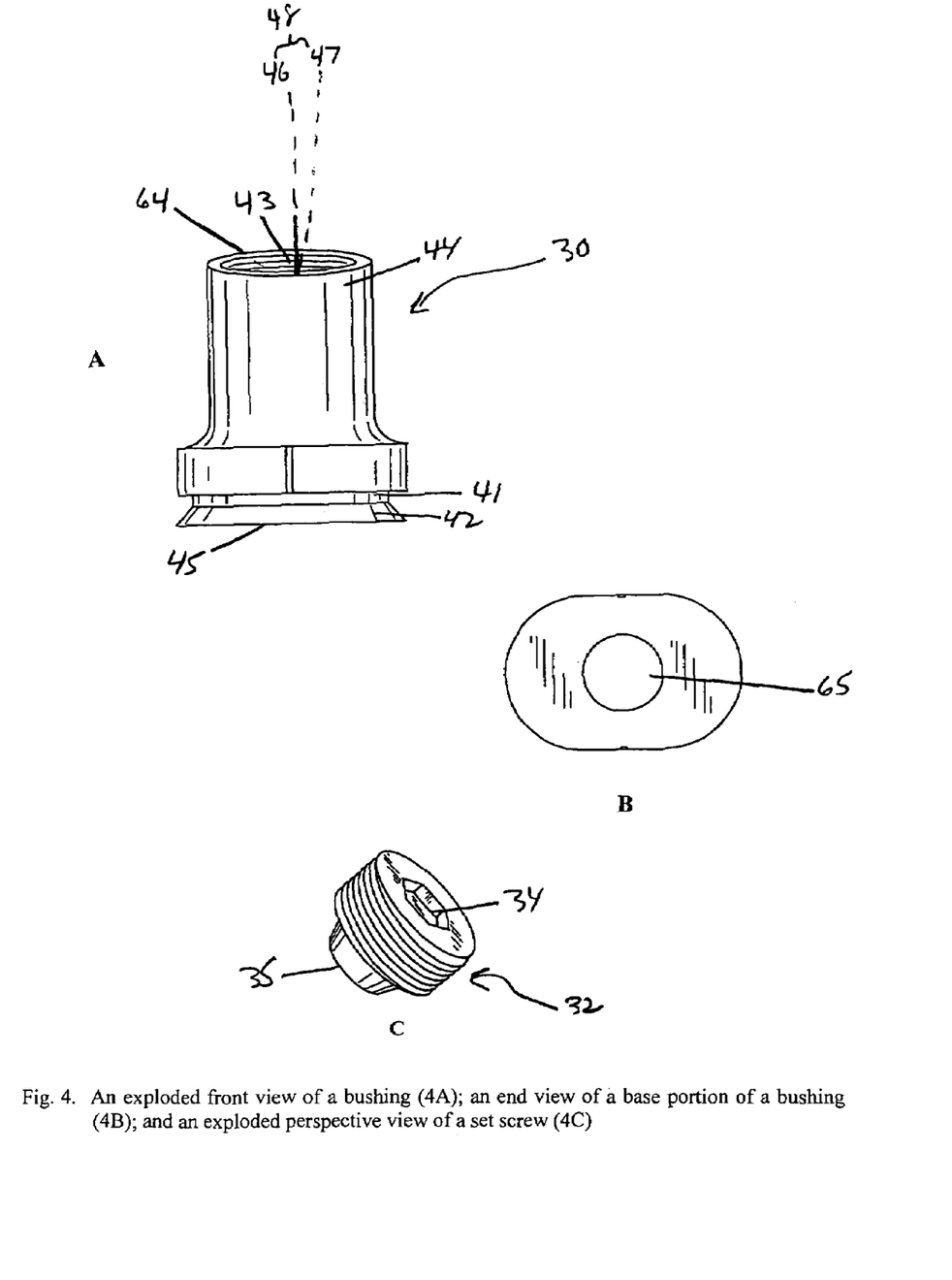
FIG. 4A is an exploded front view of a bushing.
FIG. 4B is an end view of a base portion of a bushing.
FIG. 4C is an exploded perspective view of a set screw.

As shown in FIG. 4, a bushing, having a bore 43 therethrough and an upper portion 44 defining a major bore aperture 64 therein and a base portion 45 defining a minor bore 65 therein, is configured for sliding engagement along the engagement surface 25 of the intercondylar region 24. Preferably, both the major bore aperture 64 and the minor bore 65 are threaded. The base portion 45 of the bushing 30 includes mating surfaces 41. The mating surfaces 41 can be any shape or size of surface (within the limitations of the femoral component 15 and within anatomical limitations of the patient) which allow for engagement with the engagement surface 25 of the intercondylar region 24 of the femoral component 15, such as rectangular grooves. Preferably, the mating surfaces 41 are in the form of dovetails 42. The base portion 45 of the bushing 30 may, but need not, be the same length or width as the upper portion 44. The bushing 30 can be shaped in a variety of configurations. Preferably, the bushing 30 is symmetrical so that it can be used in either the right or left knee, with a surgeon only having to rotate the bushing 30 by 180° to have it match the valgus angle for either the right or left knee.

The bore 43 of the bushing 30 extends from the upper portion 44 to the base portion 45 of the bushing 30. The diameter of the bore 43 is wide enough to allow a locking member 32 to pass through the bore 43 from the upper portion 44 to the base portion 45, even if the bushing 30 is canted at an acute angle. However, the locking member 32 is configured to fit snugly in the base portion 45 of the bushing 30. Therefore, the diameter of the bore 43 need not be constant. For example, the bore 43 can be wider at the upper portion 44 than at the base portion 45. Additionally, the bore 43 preferably is threaded for receiving the locking member 32. The minor bore 65 of the bushing 30 is for receiving the locking member 32. The major bore aperture 64 is configured for receiving the femoral stem 20.

As shown in FIGS. 3B and 4A, the bushing 30 preferably is canted in the medial/lateral direction at an acute angle so as to have a canting angle 48. The base portion 45 of the bushing 30, including the mating surfaces 41, defines a central axis 47 offset from the plane of symmetry 46 at an acute angle, i.e., the canting angle 48. The canting angle 48 is designed to match substantially a patient's valgus angle. Preferably, the canting angle 48 is in the range of 0 to about 9 degrees. More preferably, the canting angle 48 is one of 0, 3, 5 or 7 degrees. As shown in FIG. 2A, the femoral component 15 is configured such that a plane of symmetry 46 is defined between the condylar portions 23 in the anterior-posterior direction.

Figure 1:
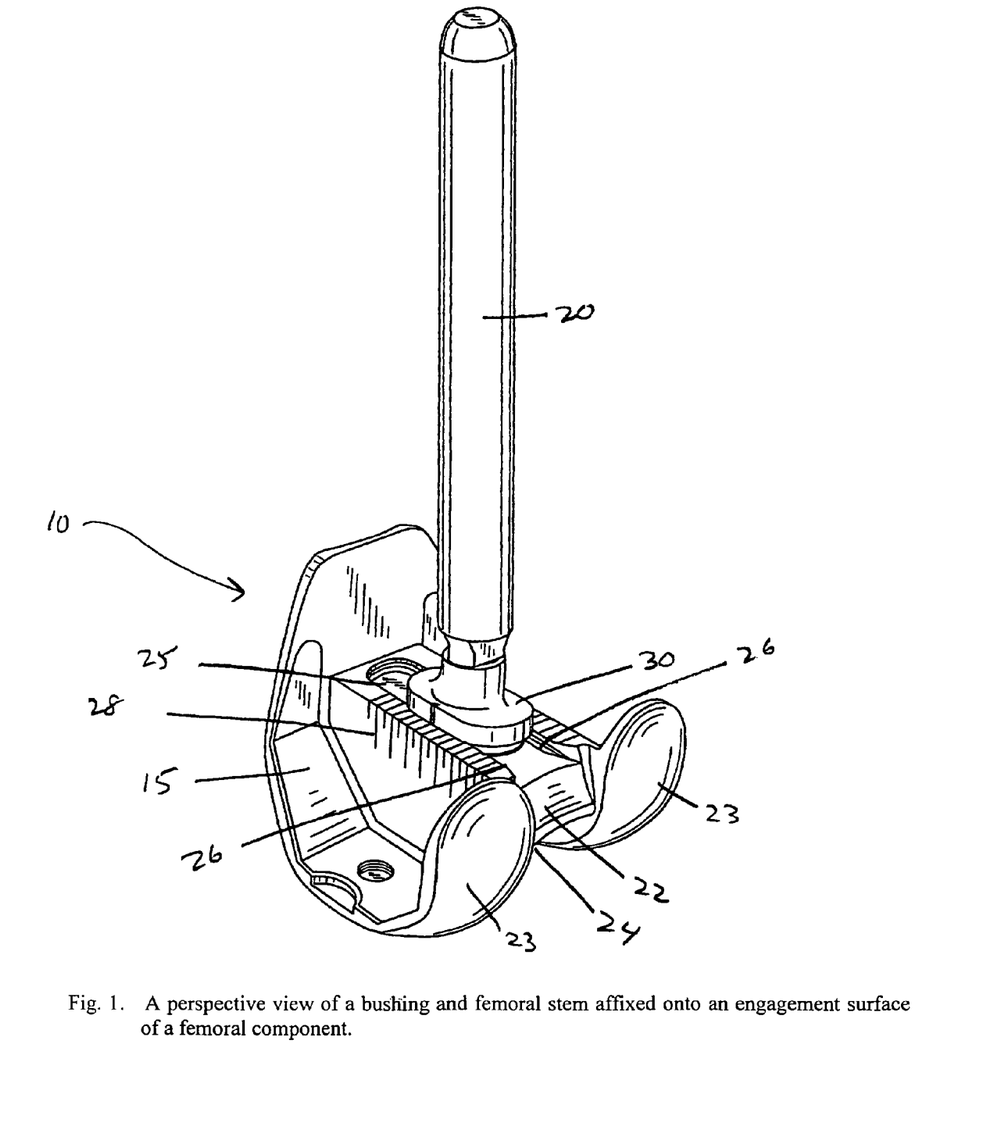
FIG. 1 is a perspective view of a bushing and femoral stem affixed onto an engagement surface of a femoral component.
Figure 2:
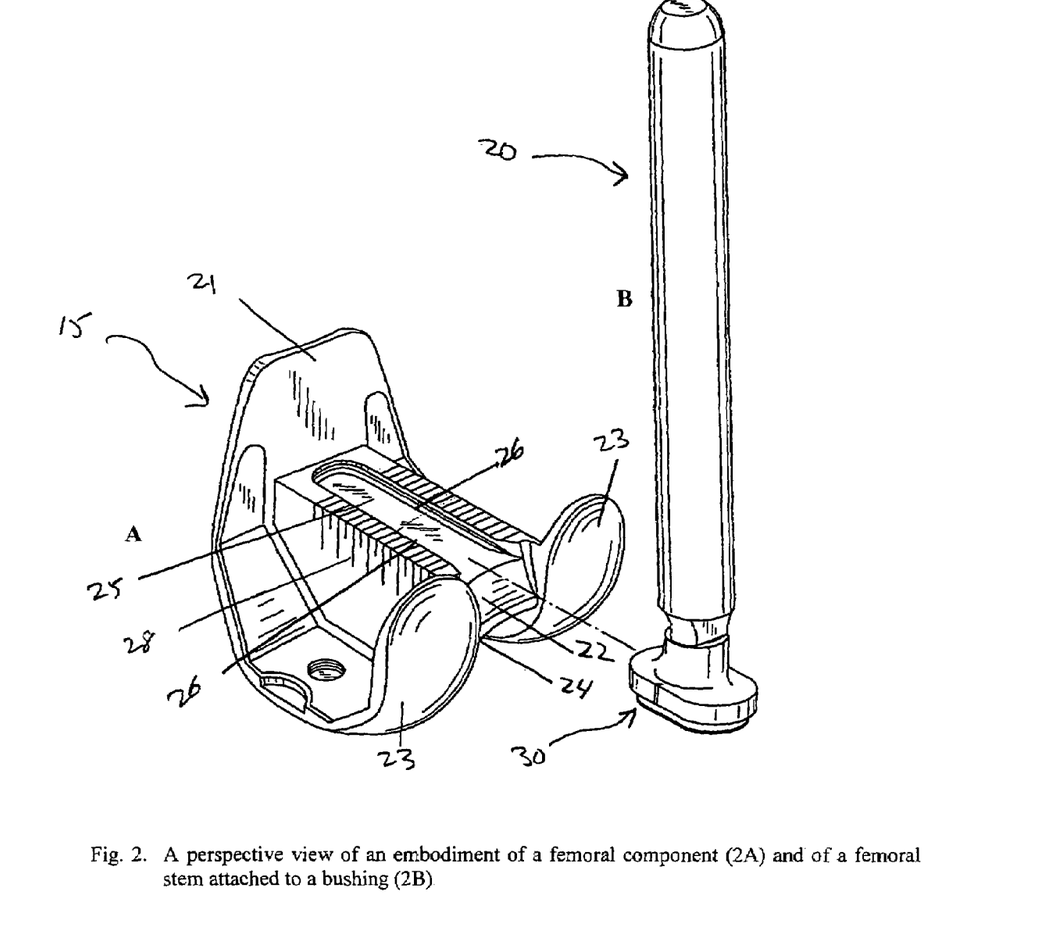
FIG. 2A is a perspective view of an embodiment of a femoral component.
FIG. 2B is a perspective view of a femoral stem attached to a bushing.
Figure 3:
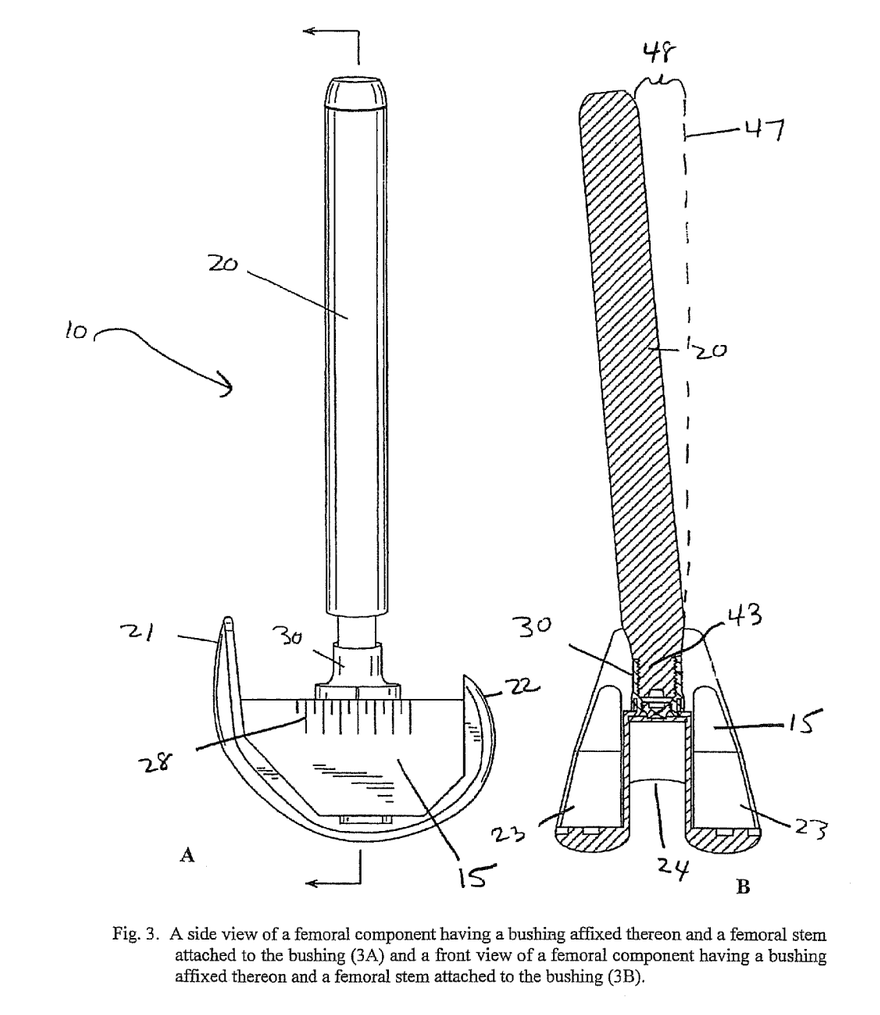
FIG. 3A is a side view of a femoral component having a bushing affixed thereon and a femoral stem attached to the bushing.
FIG. 3B is a front view of a femoral component having a bushing affixed thereon and a femoral stem attached to the bushing.

FIGS. 1, 3A and 3B illustrate the engagement of the bushing 30 to the femoral component 15, in which the bushing 30 is inserted into a sliding engagement with the femoral component 15. The engagement surface 25 in the intercondylar region 24 of the femoral component 15 mates with the mating surfaces 41 of the bushing 30 in order to allow the mating surfaces 41 to slide across the engagement surface 25. Preferably, the engagement surface 25 comprises opposing rails 26 that are complementary to the mating surfaces 41, which preferably form dovetails 42. The bushing is slideably inserted from the posterior surface 22 of the femoral component 15 toward the anterior surface 21 and is affixed at a position bearing the same incremental marking 28 value as that which was noted by the surgeon from the position of the cutting block 40 incremental marking 58 value.

After the correct anterior/posterior position of the bushing 30 is located on the femoral component 15, the bushing 30 is locked into place on the femoral component 15 by means of the locking member 32 (FIG. 4C). The locking member 32 is inserted into the major bore aperture 64 of the bushing 30. The locking member 32 then travels from the upper portion 44 of the bushing 30 to the base portion 45 of the bushing 30. Once the locking member 32 is at the base portion 45 of the bushing 30, the locking member 32 can be tightened by a device, such as a torque wrench, in order to lock the position of the bushing 30 on the femoral component 15. The locking member 32 can be threaded on the outside so as to provide a mating surface with a complementary surface of the minor bore 65 of the bushing 30 (FIG. 4B). The inside of the locking member 32 or a surface on the locking member 32 is configured for releasable engagement with the tightening device. A commercial embodiment of the prosthesis preferably would be factory assembled so that the locking member 32 is preplaced in the minor bore 65 of the bushing 30. After the surgeon places the bushing 30 in the predetermined anterior-posterior location using the value of the incremental marking 58 on the cutting block 40, the already in-place locking member 32 can be tightened to lock the bushing. The locking member 32 preferably is a set screw which preferably is rounded and has a proximal end 34 and a distal end 35. The proximal end 34 has a surface that allows the set screw to be tightened intraoperatively by means of a device, such as a torque wrench. The distal end 35 of the set screw has a surface that, in use, extends beyond the base portion 45 of the bushing 30 so that upon tightening, the distal end 35 contacts the femoral component 15 to form a pressure fitting against the femoral component 15, which locks the predetermined position of the bushing 30 against the femoral component 15.

The femoral component 15 including the femoral stem 20 is shown in FIGS. 1, 3A and 3B. The femoral stem 20 is configured for insertion, in use, into the medullary canal of a distal femur of a patient (not shown). The femoral stem 20 can be linear or can be curved along its longitudinal axis (FIG. 2B), depending upon the anatomy of the intramedullary canal of the patient's femur. Additionally, the cross-sectional configuration of the femoral stem 20 can have any one of a number of shapes, although a circular cross-sectional configuration is preferred. Furthermore, the femoral stem 20 can have one of a variety of different combinations of length and width. The femoral stem 20 is configured for insertion, in use, into the femoral canal of the patient, and the upper portion 44 of the bushing 30 is configured for secure attachment to the femoral stem 20 so as to align the femoral stem 20 at a canting angle 48 along the central axis 47 of the upper portion of the bushing 30.

Thus, the present invention comprised of the revision knee implant 10 and cutting block system enables a surgeon to maximally position the cutting block 40 adjacent to a distal femur of a patient, to surgically cut the femur to substantially match the contours of the femoral component 15, and then to properly position and align the femoral prosthesis to the distal femur of the patient using the corresponding incremental markings 58, 28 on the cutting block 40 and femoral component 15, respectively, in order to provide intimate contact of the femoral prosthesis with the femur of the patient, in which no gaps are present between the femur and the anterior or posterior ends of the prosthesis. Additionally, the combination of the anterior-posterior positioning freedom and the range of valgus angle positions provided by the present invention allows the axis of the femoral stem 20 to be aligned properly within the femoral canal of the patient in both the anterior-posterior position and along the patient's valgus angle. Furthermore, the femoral prosthesis of the present invention allows the bushing 30 and, therefore, the femoral stem 20 when attached, to be moved through and locked into any position along the anterior-posterior length of the intercondylar region 24 of the femoral component 15.

The components of the revision knee femoral prosthesis can be made from any biocompatible material or materials. Suitable materials include cobalt chrome, titanium and stainless steel. Preferably, the femoral component 20 is made of titanium or cobalt chrome, the femoral stem 20 preferably is made of titanium and the locking member 32 is made of titanium or cobalt chrome. Similarly, the components of the cutting block can be made from any material or materials, which include, without limitation, stainless steel and alloys of stainless steel.

Those of ordinary skill in the art will appreciate that various changes in the detail, methods, materials and arrangements of parts which have been described herein and illustrated in order to explain the nature of the invention may be made by the skilled artisan within the principle and scope of the invention as expressed in the appended claims.

The invention claimed is:

1. In a system for providing revision knee surgery, and specifically the surgical implantation of a femoral component of a revision knee, the method comprising:

reaming a distal femur of a patient to enlarge an intramedullary canal therein;

inserting in said intramedullary canal a trial stein attached to a cutting block, said cutting block having a front surface and a back surface and further having a first set of incremental markings on the front surface thereof, wherein said trial stem is hingedly attached to said back surface of said cutting block by a cutting block bushing, wherein said trial stem is able to rotate through about 10 degrees laterally around a longitudinal axis running perpendicularly to the back surface of said cutting block, wherein said cutting block is able to adjust in an anterior-posterior direction by means of an adjustment screw, said adjustment screw being threadably engaged to said cutting block bushing;

adjusting said cutting block by means of said adjustment screw to position said cutting block adjacent a maximal area as possible of said distal femur to an adjustment position;

reading and noting said adjustment position by means of said first set of incremental markings on said front surface of said cutting block;

using said cutting block to cut the distal femur to fit a femoral component bearing incremental markings thereon;

removing said cutting block and said trial stem from said distal femur;

affixing a bushing having an upper portion and a base portion to said femoral component bearing a second set of incremental markings, wherein said second set of incremental markings correspond to said first set of incremental markings, to said adjustment position by means of said second set of incremental markings;

attaching a femoral stein to said bushing; and implanting said femoral stem and said femoral component into said distal femur.

2. The method of claim 1, wherein the cutting block has a plurality of cutting slots defined therein.

3. The method of claim 2, wherein the cutting slots are comprised of an anterior resection slot, an anterior chamfer slot, a posterior chamfer slot and three posterior resection slots.

4. The method of claim 1, wherein the bushing is locked onto the femoral component by means of a locking member.

5. The method of claim 4, wherein the locking member is a set screw.

6. The method of claim 1, wherein said base portion of said bushing has mating surfaces.

7. The method of claim 6, wherein said mating surfaces are in the form of dovetails.

8. The method of claim 1, wherein the femoral component has spaced apart condylar portions defining an intercondylar region therebetween, said intercondylar region having an elongate engagement surface extending in an anterior-posterior direction.

9. The method of claim 8, wherein the bushing is configured for sliding engagement with said engagement surface of said intercondylar region for movement in said anterior-posterior direction.

10. The method of claim 8, wherein said femoral component is configured such that a plane of symmetry is defined between the condylar portions in the anterior-posterior direction.

11. The method of claim 10, wherein said upper portion of said bushing defines a central axis offset from the plane of symmetry at an acute angle.

12. The method of claim 11, wherein said upper portion of said bushing is offset to a degree to substantially match the valgus angle of the patient.

13. The method of claim 12, wherein said upper portion of said bushing is configured for secure attachment to said femoral stem to align said femoral stem at an acute angle along the central axis of said upper portion.

14. The method of claim 13, wherein said acute angle is a canting angle ranging from between about 0 to 9 degrees.

15. The method of claim 13, wherein said acute angle is a canting angle of one of 0, 3, 5 or 7 degrees.

* * * * *

UNITED STATES PATENT AND TRADEMARK OFFICE
CERTIFICATE OF CORRECTION

PATENT NO. : 7,628,794 B2  Page 1 of 1
APPLICATION NO. : 11/100349
DATED : December 8, 2009
INVENTOR(S) : Stumpo et al.

It is certified that error appears in the above-identified patent and that said Letters Patent is hereby corrected as shown below:

Column 7, Line 3, Claim 1, "a trial stein" should read -- a trial stem --

Column 7, Line 26, Claim 1, "a femoral stein" should read -- a femoral stem --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,628,794 B2
APPLICATION NO. : 11/100349
DATED : December 8, 2009
INVENTOR(S) : Stumpo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1159 days.

Signed and Sealed this

Second Day of November, 2010

David J. Kappos
*Director of the United States Patent and Trademark Office*